United States Patent
Kim et al.

(10) Patent No.: US 9,638,625 B2
(45) Date of Patent: May 2, 2017

(54) APPARATUS FOR FILTERING SPECIES

(75) Inventors: Ansoon Kim, Mountain View, CA (US); Zhiyong Li, Foster City, CA (US); Wei Wu, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 289 days.

(21) Appl. No.: 14/345,277

(22) PCT Filed: Oct. 27, 2011

(86) PCT No.: PCT/US2011/058130
§ 371 (c)(1),
(2), (4) Date: Mar. 17, 2014

(87) PCT Pub. No.: WO2013/062554
PCT Pub. Date: May 2, 2013

(65) Prior Publication Data
US 2014/0347661 A1    Nov. 27, 2014

(51) Int. Cl.
*G01J 3/44* (2006.01)
*G01N 21/05* (2006.01)
(Continued)

(52) U.S. Cl.
CPC .......... *G01N 21/05* (2013.01); *G01N 21/554* (2013.01); *G01N 21/658* (2013.01); *B82Y 20/00* (2013.01);
(Continued)

(58) Field of Classification Search
CPC .... G01N 21/05; G01N 21/554; G01N 21/658; G01N 33/491; G01N 2001/4088; G01N 2021/651; B82Y 20/00
See application file for complete search history.

(56) References Cited

U.S. PATENT DOCUMENTS 7,309,385 B2    12/2007  Hong et al.
7,427,343 B2    9/2008   Han et al.
(Continued)

FOREIGN PATENT DOCUMENTS

CN    101400976    4/2009
CN    101792112    8/2010
(Continued)

OTHER PUBLICATIONS

Kim, Ansoon, et al., Study of Molecular Trapping Inside Gold Nanofinger Arrays on Surface-Enhanced Raman Substrates, JACS, Apr. 26, 2011, pp. 8234-8239, vol. 133.
(Continued)

*Primary Examiner* — Hina F Ayub
(74) *Attorney, Agent, or Firm* — Mannava & Kang, P.C.

(57) ABSTRACT

An apparatus for filtering species in a fluid includes a body having a first side and a second side, a first set of nano-fingers positioned on the body near the first side, a second set of nano-fingers positioned on the body closer to the second side than the first set of nano-fingers, wherein the nano-fingers in the second set of nano-fingers are arranged on the body at a relatively more densely than the nano-fingers in the first set of nano-fingers, and a cover positioned over the first set of nano-fingers and the second set of nano-fingers to form a channel with the body within which the first and second sets of nano-fingers are positioned.

13 Claims, 4 Drawing Sheets

(51) Int. Cl.
*G01N 21/65* (2006.01)
*G01N 21/552* (2014.01)
*G01N 33/49* (2006.01)
*G01N 1/40* (2006.01)
*B82Y 20/00* (2011.01)

(52) U.S. Cl.
CPC ... *G01N 33/491* (2013.01); *G01N 2001/4088* (2013.01); *G01N 2021/651* (2013.01)

(56) References Cited

U.S. PATENT DOCUMENTS

| | | | |
|---|---|---|---|
| 7,476,501 | B2 | 1/2009 | Chan et al. |
| 7,898,658 | B2 | 3/2011 | Moskovits et al. |
| 2002/0125192 | A1 | 9/2002 | Lopez et al. |
| 2003/0187237 | A1 | 10/2003 | Chan et al. |
| 2004/0135997 | A1* | 7/2004 | Chan ............ C12Q 1/6825 356/301 |
| 2006/0189858 | A1* | 8/2006 | Sterling ........... A61B 5/1427 600/310 |
| 2007/0153267 | A1 | 7/2007 | Wang et al. |
| 2008/0149479 | A1 | 6/2008 | Olofsson et al. |
| 2009/0232870 | A1 | 9/2009 | Srivastava et al. |
| 2010/0050866 | A1 | 3/2010 | Yu et al. |
| 2010/0183875 | A1 | 7/2010 | Mao et al. |
| 2011/0053794 | A1 | 3/2011 | Zhang |
| 2011/0116089 | A1 | 5/2011 | Schmidt et al. |
| 2011/0188034 | A1 | 8/2011 | Stuke et al. |
| 2012/0154791 | A1* | 6/2012 | Kuo .................. G01J 3/0227 356/51 |
| 2012/0164745 | A1* | 6/2012 | Fu ................... H01F 1/0063 436/164 |
| 2012/0178640 | A1* | 7/2012 | Strano ................ B82Y 5/00 506/9 |
| 2012/0212732 | A1* | 8/2012 | Santori ............. B82Y 20/00 356/301 |
| 2016/0003744 | A1* | 1/2016 | Chou ............... G01N 21/6486 435/5 |

FOREIGN PATENT DOCUMENTS

| | | |
|---|---|---|
| CN | 102046274 | 5/2011 |
| JP | 2005061997 | 3/2005 |
| JP | 2010284649 | 12/2010 |
| JP | 2011-208993 | 10/2011 |
| WO | WO-2010126686 | 11/2010 |

OTHER PUBLICATIONS

Hu, Min, et al., Gold Nanofingers for Molecule Trapping and Detection, American Chemical Society, Dec. 31, 2010, pp. 12820-12822.

International Search Report and Written Opinion, KIPO, May 1, 2012. Hewlett-Packard Development Company, L.P., PCT Application No. PCT/US2011/058130.

* cited by examiner

APPARATUS FOR FILTERING SPECIES

BACKGROUND

Raman scattering optical spectroscopy employs an emission spectrum or spectral components thereof produced by inelastic scattering of photons by an internal structure of the material being illuminated. These spectral components contained in a response signal (for instance, a Raman signal) are to facilitate determination of the material characteristics of an analyte species including identification of the analyte.

The Raman signal level or strength is often significantly enhanced by using a Raman-active material (for instance, Raman-active surface), however. For instance, the Raman scattered light generated by a compound (or ion) adsorbed on or within a few nanometers of a structured metal surface can be $10^3$-$10^{12}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection. Engineers, physicists, and chemists continue to seek improvements in systems and methods for performing SERS.

BRIEF DESCRIPTION OF THE DRAWINGS

Features of the present disclosure are illustrated by way of example and not limited in the following figure(s), in which like numerals indicate like elements, in which.

DETAILED DESCRIPTION

Figure 1A:
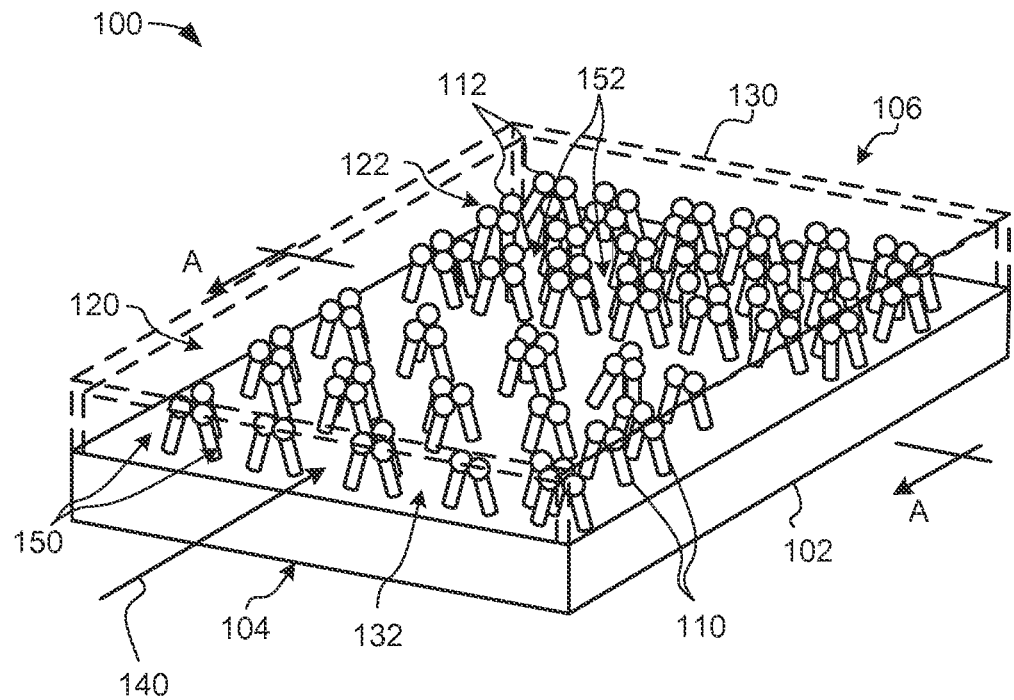
FIG. 1A shows an isometric view of an apparatus for filtering species in a fluid, according to an example of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared and ultra-violet portions of the electromagnetic spectrum.

Disclosed herein is an apparatus for filtering species in a fluid and for use in a sensing operation. Also disclosed herein are a method for fabricating the apparatus and a method for performing a sensing operation using the apparatus. The apparatus includes a body having a first side and a second side, a first set of nano-fingers positioned on the body near the first side, and a second set of nano-fingers positioned on the body closer to the second side than the first set of nano-fingers, in which the nano-fingers in the second set of nano-fingers are arranged at a relatively higher density level than the nano-fingers in the first set of nano-fingers. The apparatus also includes a cover positioned over the first set of nano-fingers and the second set of nano-fingers to form a channel with the body within which the first and second sets of nano-fingers are positioned.

According to an example, the fluid sample flows through the apparatus 100 from the first side to the second side. While the fluid sample flows through the apparatus, the larger sized species in the fluid sample than a gap size between the first set of nano-fingers are unable to pass through the first set of nano-fingers and are thus filtered from the remainder of the fluid sample. Likewise, at least some of the species become trapped in the second set of nano-fingers, and so forth. The remaining portions of the fluid sample have therefore been filtered and the remaining species are the ones that are sufficiently small to pass through each of the sets of nano-fingers having increasing density levels and therefore, smaller gaps.

The apparatus is also to be used in a sensing device, in which the sensing device is to perform a sensing operation on the species filtered by the apparatus. In certain implementations, the sensing device is also to perform the sensing operation while the species are contained in the apparatus, for instance, by performing the sensing operation on at least one section of the apparatus. As described in greater detail herein below, the sensing device comprises an integrated and portable device. As such, the sensing device is usable to perform sensing operations on fluid samples at locations where the fluid samples are collected, for instance. In other words, the sensing device disclosed herein enables point-of-care diagnostics to be performed on the fluid samples.

According to an example, at least some of the nano-fingers contained in the apparatus 100 include Raman-active material nano-particles. The use of multiple nano-fingers having Raman-active material nano-particles as disclosed herein generally enhances the electromagnetic field generation and therefore the Raman scattering of light from the species to be tested. In other words, the closely positioned Raman-active material nano-particles on the nano-fingers enable hot-spots to have a larger electric field strength as compared with Raman-active material nano-particles that have simply been placed on the component layer because, for instance, the use of the nano-fingers enables the formation of well controlled arrangement of nano-particles with relatively small (less than about 10 nm wide) gaps between adjacent nano-particles.

According to a particular example, the apparatus and sensing device disclosed herein are used as a biosensor. More particularly, for instance, the apparatus is used to filter out species in a relatively small amount of a blood sample. In this example, the first set of nano-fingers arranged at a relatively lower density level is able to filter out cells from the blood sample, such that sensing operations may be performed on the remaining components of the blood sample. As such, the apparatus disclosed herein is able to replace relatively large and expensive centrifuges, which are typically used to filter out cells from blood samples.

With reference first to FIG. 1A, there is shown an isometric view of an apparatus 100 for filtering species in a fluid, according to an example. The apparatus 100 is depicted as including a body 102 having a first side 104 and a second side 106. The apparatus 100 is also depicted as including a plurality of nano-fingers 110 positioned on a surface of the body 102. A cover 130 is also depicted as being positioned over the nano-fingers 110 to form a channel with the body 102 within which the nano-fingers 110 are positioned.

As shown in FIG. 1A, the nano-fingers 110 are formed in separate sets 120, 122 along a length of the body 102. More particularly, a first set 120 of nano-fingers 110 is positioned closer to the first side 104 of the body 102 and a second set 122 of nano-fingers 110 is positioned closer to the second side 106 of the body 102. The nano-fingers 110 in the first set 120 are arranged on the body 102 relatively less densely than the nano-fingers 110 in the second set 122. In this regard, gaps 150 between the nano-fingers 110 in the first set 120 are relatively larger than gaps 152 between the nano-fingers 110 in the second set 122. As a fluid sample is introduced into the apparatus 100 through the first side 104 of the body 102 as noted by the arrow 140, relatively smaller species contained in the fluid sample are able to pass through the first set 120 of nano-fingers 110, while relatively larger species contained in the fluid sample are trapped by the nano-fingers 110 in the first set 120.

As also shown in FIG. 1A, the nano-fingers 110 in each of the first and second sets 120 and 122 include Raman-active material nano-particles 112. The Raman-active material nano-particles 112 generally enable sensing operations, such as, surface enhanced Raman spectroscopy (SERS), enhanced fluorescence, enhanced luminescence, etc., to be performed on species positioned on or near the nano-fingers 110. The sensing operations are performed on the species to detect molecules in fluid samples. In one example, the sensing operations are performed on species on or near the first set 120 of nano-fingers 110 and/or species on or near the second set 122 of nano-fingers 110. In another example, the sensing operations are performed on only on the species on or near second set 122 of nano-fingers 110. Various manners in which the sensing operations are performed are discussed in greater detail herein below.

The cover 130 has been depicted with dashed lines to indicate that the cover is formed out of an optically transparent material, such as, glass, plastic materials including polymethylmethacrylate (PMMA), polydimethylsiloxane (PDMS), cyclic olefin copolymer (COC), perfluoropolyethers (PFPEs), thermoset polyester (TPE), polycarbonate (PC), polystyrene (PS), polyvinylchloride (PVC), polyethyleneterephthalate glycol (PETG), polyimide, SU-8, etc, or a combination of these materials. The cover 130 may be attached to the body 102 through any suitable attachment mechanism that enables a substantially fluid-tight bond and body 102 and the cover 130, such as, heat bonding, adhesives, etc. In other instances, the cover 130 is removably attached to the body 102. In any regard, the cover 130 forms a channel through which fluid samples are directed through the nano-fingers 110. In addition, the cover 130 is spaced in relatively close proximity to the nano-fingers 110 to substantially prevent relatively larger amounts of sample fluid than are allowed to pass through the nano-fingers 110 to pass between the nano-fingers 110 and the cover 130. In another regard, the cover 130 enables light to be directed onto the Raman-active material nano-particles 112 and for Raman scattered light emitted from the species of the fluid sample to be directed out of the apparatus 100, as discussed in greater detail herein below.

Although the body 102 and the cover 130 have been depicted as having a generally rectangular cross-sectional shape, the body 102 and the cover 130 may have other cross-sectional shapes, such as, circular, triangular, etc. According to an example, the apparatus 100 has a thickness in the range of about 10 μm to about 20 mm, has a length in the range from about 1 mm to about 200 mm, and has a width in the range from about 100 μm to about 30 mm. In one example, the apparatus 100 has sufficiently large dimensions, for instance, to enable the channel formed between the body 102 and the cover 130 to receive sample fluid and for the sample fluid to flow through the apparatus 100. In addition, the apparatus 100 has sufficiently small dimensions, for instance, to enable the fluid sample to move through the apparatus 100 via capillary forces interacting on the fluid sample. Examples of suitable materials for the body 102 include silicon, silicon nitride, glass, paper, plastic, polymer, $SiO_2$, $Al_2O_3$, gold, silver, copper, platinum, aluminum, etc., or a combination of these metals in the form of alloys, etc.

The nano-fingers 110 are formed of a relatively flexible material to enable the nano-fingers 110 to be laterally bendable, for instance, to enable tips of the nano-fingers 110 to move toward each other, as discussed in greater detail herein below. Examples of suitable materials for the nano-fingers 110 include polymer materials, such as, UV-curable or thermal curable imprinting resist, polyalkylacrylate, polysiloxane, polydimethylsiloxane (PDMS) elastomer, polyimide, polyethylene, polypropelene, fluoropolymer, etc., or any combination thereof, metallic materials, such as, gold, silver, aluminum, etc., semiconductor materials, etc., and combinations thereof.

The nano-fingers 110 are attached to the surface of the body 102 through any suitable attachment mechanism. For instance, the nano-fingers 110 are grown directly on the body 102 surface through use of various suitable nanostructure growing techniques. As another example, the nano-fingers 110 are integrally formed with the body 102. In this example, for instance, a portion of the material from which the body 102 is fabricated is etched or otherwise processed to form the nano-fingers 110. In a further example, a separate layer of material is adhered to the body 102 surface and the separate layer of material is etched or otherwise processed to form the nano-fingers 110. In various other examples, the nano-fingers 110 are fabricated through a nanoimprinting or embossing process in which a template of relatively rigid pillars is employed in a multi-step imprinting process on a polymer matrix to form the nano-fingers 110. Various other processes, such as, etching, and various techniques used in the fabrication of micro-electromechanical systems (MEMS) and nano-electromechanical systems (NEMS) may also be used to fabricate the nano-fingers 110.

A nano-finger 110 is defined, for instance, as an elongated, nanoscale structure having a length (or height) that exceeds by more than several times a nanoscale cross sectional dimension (for instance, width) taken in a plane perpendicular to the length (for instance, length>3×width). In general, the length is much greater than the width or cross sectional dimension to facilitate bending of the nano-finger 110 laterally onto one or more neighboring nano-fingers 110. In some examples, the length exceeds the cross sectional dimension (or width) by more than a factor of about 5 or 10. For example, the width may be about 100 nanometers (nm) and the height may be about 500 nm. In another example, the width at the bases of the nano-fingers 110 may range between about 10 nm and about 1 micrometer (μm) and the length may range between about 50 nm and 2 μm. In other examples, the nano-fingers 110 are sized based upon the types of materials used to form the nano-fingers 110. Thus, for instance, the more rigid the material(s) used to form the nano-fingers 110, the less the width of the nano-fingers 110 may be to enable the nano-fingers 110 to be laterally collapsible. In further examples, the nano-fingers 110 may form ridges in which two of three dimensions (for instance, length and height) exceed by more than several times a nanoscale cross sectional dimension (for instance, width). The nano-fingers 110 may equivalently be referenced as nanopoles or nanopillars.

The nano-fingers 110 have been depicted as having substantially cylindrical cross-sections. It should, however, be understood that the nano-fingers 110 may have other shaped cross-sections, such as, for instance, rectangular, square, triangular, etc. In addition, or alternatively, the nano-fingers 110 may be formed with one or more features, such as, notches, bulges, etc., to substantially cause the nano-fingers 110 to be inclined to collapse in particular directions. Thus, for instance, two or more adjacent nano-fingers 110 may include the one or more features to increase the likelihood that the nano-fingers 110 collapse toward each other. Various manners in which the nano-fingers 110 may be collapsed are described in greater detail herein below.

The apparatus 100 has been depicted with a relatively small number of nano-fingers 110 for purposes of illustration. In operation, the apparatus 100 may include a relatively large number of nano-fingers 110 in each of the sets 120, 122. For instance, each of the sets 120, 122 of nano-fingers 110 may include hundreds to thousands of nano-fingers 110. The number of nano-fingers 110 in each of the sets 120, 122 as well as their relative spacings may depend upon the intended application of the apparatus 100.

The nano-fingers 110 are distributed on the surface in a substantially random manner or the nano-fingers 110 are arranged in a predetermined configuration. The distribution of the nano-fingers 110 in both of the sets 120, 122 of nano-fingers 110 may be selected to filter species of predetermined sizes. In either example, the nano-fingers 110 in the first set 120 are spaced at a greater distance with respect to each other than the nano-fingers 110 in the second set 122, and thus, there are a fewer number of nano-fingers 110 in the first set 120 for a same unit of space than the nano-fingers in the second set 122. In addition, or alternatively, the nano-fingers 110 in the first set 120 are relatively thinner than the nano-fingers 110 in the second set 122. In any regard, according to an example, the nano-fingers 110 in each of the sets 120, 122 are arranged with respect to each other such that the tips of at least two neighboring nano-fingers 110 are able to touch each other when the nano-fingers 110 are in a bent condition. By way of particular example, the neighboring nano-fingers 110 in each of the sets 120, 122 are positioned less than about 100 nanometers apart from each other at their respective bases.

As also shown in FIG. 1A, Raman-active material nano-particles 112 are provided on the tips of the nano-fingers 110. The Raman-active material nano-particles 112 comprise a metal, such as, gold, silver, copper, platinum, aluminum, etc., or a combination of these metals in the form of alloys, or other suitable material that is able to support surface plasmons for field enhancement for Raman scattering. In addition, the Raman-active material nano-particles 112 may be multilayer structures, for example, 10 to 100 nm silver layer with 1 to 50 nm gold over-coating, or vice versa. By definition herein, a Raman-active material is a material that facilitates Raman scattering from a sample positioned near the Raman-active material during Raman spectroscopy.

Although the Raman-active material nano-particles 112 have been depicted as being formed on all of the nano-fingers 110 in each of the sets 120, 122, it should be understood that the Raman-active material nano-particles 112 may have various alternative implementations. In one example, the Raman-active material nano-particles 112 are formed on substantially the entire heights of the nano-fingers 110. In addition or alternatively, the Raman-active material nano-particles 112 are formed on selected ones of the nano-fingers 110. Thus, in one example, the Raman-active material nano-particles 112 are formed on the nano-fingers 110 in the second set 112, while Raman-active material nano-particles 112 are not formed on the nano-fingers 110 in the first set 120.

Figure 1B:
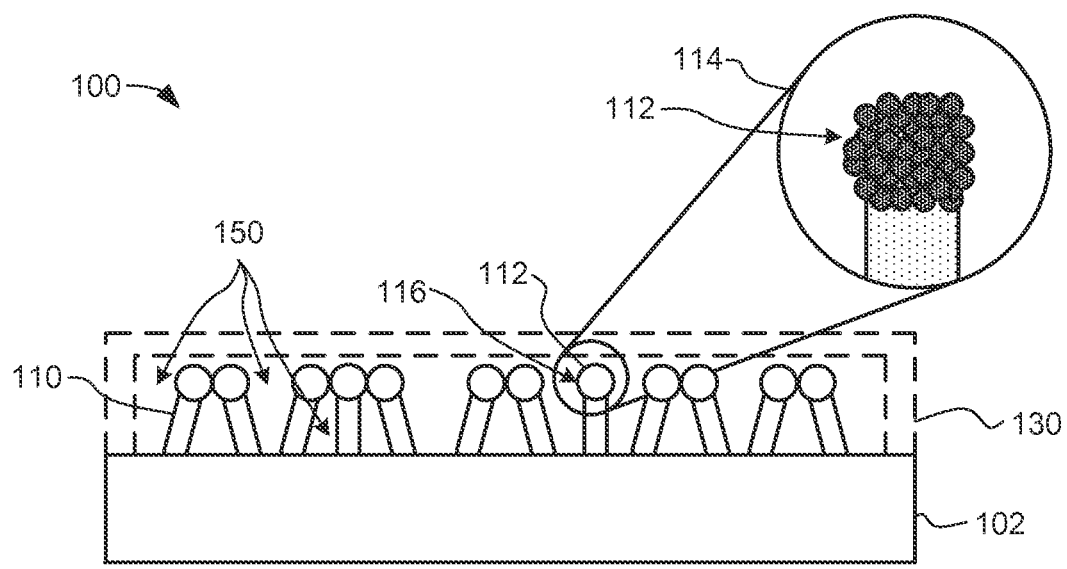
FIG. 1B shows a cross-sectional view along a line A-A, of the apparatus shown in FIG. 1A, according to examples of the present disclosure.

Turning now to FIG. 1B, there is shown a cross-sectional view along a line A-A, shown in FIG. 1A, of the apparatus 100, in accordance with an example. In addition, a free end 116 of a nano-finger 110 is magnified in an enlargement 114, which reveals that Raman-active material nano-particles 112 are disposed on the outer surface, near the tip or free end 116, of the nano-finger 110. The other nano-fingers 110 also include the Raman-active nano-particles 112 as represented by the circles on the tops or free ends 116 of the nano-fingers 110. Although the enlargement 114 depicts the Raman-active material nano-particles 112 as covering the entire tip 116 of the nano-finger 110, it should be understood that examples of the apparatus 100 may be implemented with gaps between some of the nano-particles 112. It should also be noted that examples of the apparatus 100 are not limited to nano-particles 112 disposed over just the tips of the nano-fingers 110. In other examples, the nano-particles 112 are disposed over part of or nearly the entire surface of the nano-fingers 110.

In any regard, the Raman-active material nano-particles 112 are deposited onto at least the free ends 116 of the nano-fingers 110 through, for instance, physical vapor deposition (PVD), chemical vapor deposition (CVD), sputtering, etc., of metallic material, or self-assembly of pre-synthesized nano-particles. By way of example, the angles at which the nano-particles 112 are deposited onto the free second sides 116 of the nano-fingers 110 are controlled to thereby substantially control the deposition of the nano-particles 112.

In addition, the Raman-active material nano-particles 112 may one or both of enhance Raman scattering and facilitate analyte adsorption. For instance, the Raman-active material nano-particles 112 comprise a Raman-active material such as, but not limited to, gold (Au), silver (Ag), and copper (Cu) having nanoscale surface roughness. Nanoscale surface roughness is generally characterized by nanoscale surface features on the surface of the layer(s) and may be produced spontaneously during deposition of the Raman-active material layer(s). By definition herein, a Raman-active material is a material that facilitates Raman scattering and the production or emission of the Raman signal from an analyte adsorbed on or in a surface layer or the material during Raman spectroscopy.

Although the nano-fingers 110 have been depicted in FIGS. 1A-1B as each extending at the same heights with respect to each other, it should be understood that some or all of the nano-fingers 110 may extend at various angles and heights with respect to each other. The differences in angles and/or heights between the nano-fingers 110 may be based upon, for instance, differences arising from manufacturing or growth variances existent in the fabrication of the nano-fingers 110 and the deposition of the nano-particles 112 on the nano-fingers 110, etc.

As also shown in FIG. 1B, the nano-fingers 110 are depicted in a position in which the free ends 116 of some of the nano-fingers 110 are in substantial contact with each other. According to an example, the nano-fingers 110 are fabricated to extend substantially vertically. In this example, the nano-fingers 110 are positioned with gaps of sufficiently small size to enable the free ends 116 of at least some of the nano-fingers 110 to move toward each other as a liquid introduced into the gaps evaporates, through, for instance, capillary forces applied on the free ends 116 as the liquid dries. In addition, the free ends 116 of some of the nano-fingers 110 may be in and may remain in substantial contact with each other for a period of time due to the capillary forces applied on the free ends 116 (Raman-active material nano-particles 112) during and following evaporation of a liquid in the gaps between the free ends 116. In other examples, the free ends 116 of some of the nano-fingers 110 may be maintained in the second positions through, for instance, removal of an electrostatic charge on the free ends 116. In those examples, the nano-fingers 110 may be fabricated to normally have the second position depicted in FIG. 1B and may extend substantially vertically when the electrostatic charge is applied onto the free ends 116 of the nano-fingers 110.

In any event, and in one regard, the free ends 116 of the nano-fingers 110 are caused to contact each other to create "hot spots" having relatively large electric field strengths. In other words, the relatively larger areas of the Raman-active material nano-particles 112 on adjacent nano-fingers 110 substantially increase the electric field strength attainable from the Raman-active material nano-particles 112.

Figure 1C:
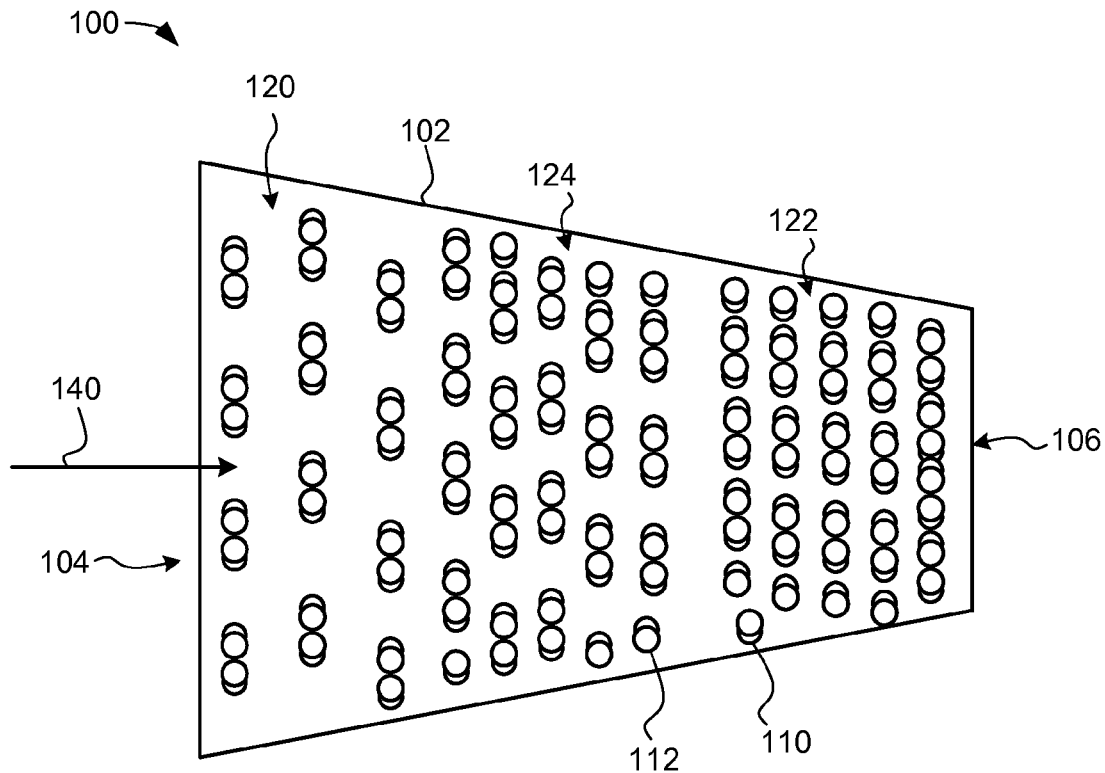
FIGS. 1C and 1D, respectively, show top view of the apparatus depicted in FIG. 1A, according to two examples of the present disclosure.
Figure 1D:
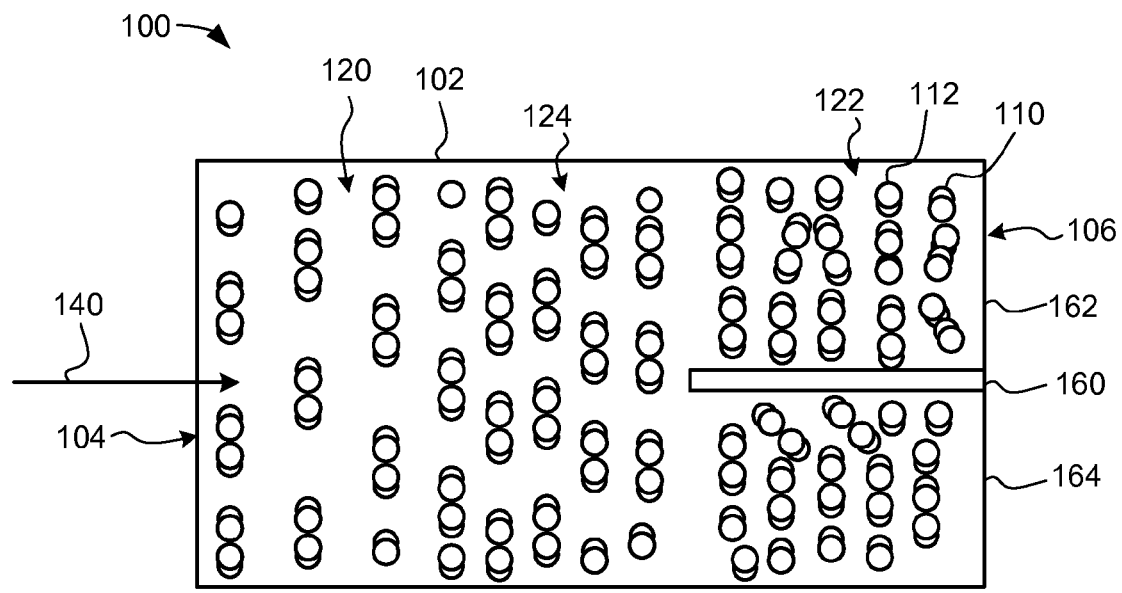

Turning now to FIGS. 1C and 1D, there are respectively shown top views of the apparatus 100 according to two examples. In FIGS. 1C and 1D, the cover 130 has not been shown for purposes of clarity. In addition, the apparatuses 100 in both FIGS. 1C and 1D are depicted as including a third set 124 of nano-fingers 110 positioned between the first set 120 and the second set 122 of nano-fingers 110. The nano-fingers 110 in the third set 124 are depicted as being arranged on the body 102 relatively more densely than the nano-fingers 110 in the first set 120, but relatively less densely than the nano-fingers 110 in the second set 122. Although not shown, the apparatus 100 may also include additional sets of non-fingers 110 that have increasing levels of densities moving from the first side 104 to the second side 106 of the apparatus 100.

In FIG. 1C, the apparatus 100 is depicted as having a tapered or funneled structure, in which the first side 104 is relatively larger than the second side 106. The size of the channel formed by the body 102 and the cover 130 therefore gradually decreases from the opening at the first side 104 to the opening at the second side 106. Alternatively, however, the apparatus 100 may have a different configuration, such as, a larger central section, a larger end section, a rounded central section, etc.

In FIG. 1D, the apparatus 100 is depicted as having a wall 160 that forms chambers 162 and 164. The wall 160 extends from a surface of the body 102 to the cover 130 to thereby divide the chambers 162 and 164 from each other. In this regard, species of the fluid sample that pass through the first set 120 and the third set 124 of nano-fingers 110 may be captured on the nano-fingers 110 in the second set 122. Additional species of the fluid sample may also pass through the second set 122 of nano-fingers 110 and out of the apparatus 100. According to an example, the nano-fingers 110 in a first chamber 162 have a different functionalization than the nano-fingers 110 in a second chamber 164. For instance, the Raman-active material nano-particles 112 formed on the nano-fingers 110 contained in the first chamber 162 are functionalized to bond with a first type of particle and the Raman-active material nano-particles 112 formed on the nano-fingers 110 contained in the second chamber 162 are functionalized to bond with a second type of particle. As such, the nano-fingers 110 in the first chamber 162 are functionalized to bond with different types of species than the nano-fingers 110 in the second chamber 164.

Although the apparatus 100 in FIG. 1D has been depicted with two chambers 162 and 164, it should be understood that the apparatus 100 may include any number of chambers without departing from a scope of the apparatus 100. In this regard, the apparatus 100 may include any number of subsets of Raman-active material nano-particles 112 that have been functionalized in various different manners to, for instance, bond with different types of species. As another example, the wall 160 may also be removed, while maintaining the different functionalizations among the subsets of Raman-active material nano-particles 112 formed on the subsets of nano-fingers 110 in the second set 122. As a further example, the Raman-active material nano-particles 112 formed on the nano-fingers 110 in the first and/or third sets 120, 124 may have different functionalizations as compared with the Raman-active material nano-particles 112 formed on the nano-fingers 110 in the second set 122. As a yet further example, subsets of the Raman-active material nano-particles 112 formed on the nano-fingers 110 in the first set 120 may have different functionalizations with respect to each other. Likewise, subsets of the Raman-active material nano-particles 112 formed on the nano-fingers 110 in the third set 124 may have different functionalizations with respect to each other.

Figure 2:
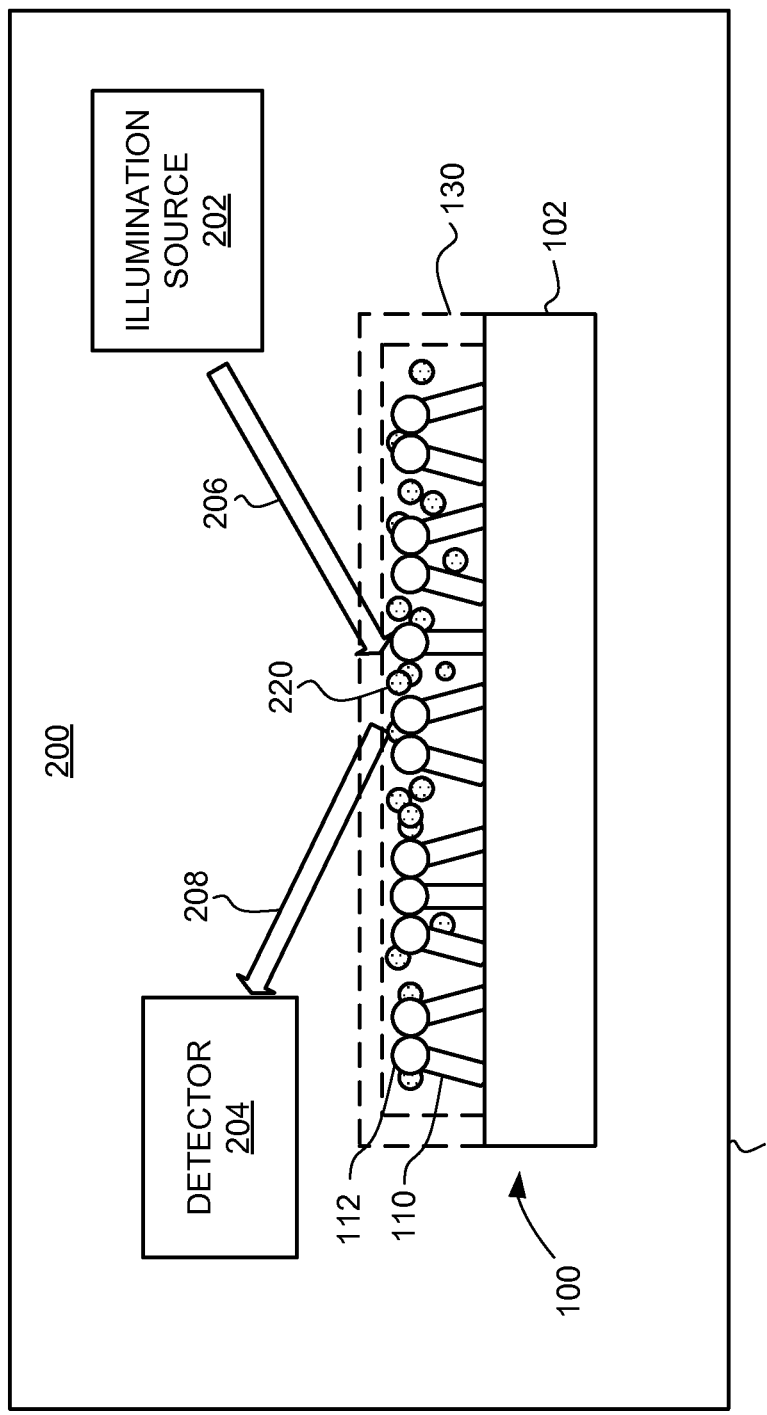
FIG. 2 shows a block diagram of a sensing device for use in a sensing operation, according to an example of the present disclosure.

With reference now to FIG. 2, there is shown a block diagram of a sensing device 200 for use in a sensing operation, according to an example. As shown in FIG. 2, the sensing device 200 includes the apparatus 100 depicted in FIGS. 1A-1D. In this regard, the sensing device 200 is to be used following collection onto the nano-fingers 110 of species 220 to be tested. In other words, the sensing device 200 is to perform a sensing operation on the Raman-active material nano-particles 112 and the species 220 following filtering of a fluid sample containing the species 220. In this regard, the portion of the apparatus 100 depicted in FIG. 2 comprises a section of the second set 122 of the nano-fingers 110. Alternatively, however, the depiction in FIG. 2 of the apparatus 100 may be of other sections of the apparatus 100.

The sensing device 200 is also depicted as including an illumination source 202 and a detector 204. The species 220 to be tested are also depicted as being positioned in contact with and in close proximity to the Raman-active material nano-particles 112. According to an example, the relative position of the apparatus 100 and the illumination source 202 and the detector 204 is to be modified to thereby enable testing to be performed on various locations of the apparatus 100. In this example, the apparatus 100 is movable with respect to the sensing device 200, the sensing device 200 is movable with respect to the apparatus 100, or both.

The illumination source 202 is depicted as emitting electromagnetic radiation, as represented by the arrow 206, which comprises, for instance, light, through the cover 130 and onto the Raman-active material nano-particles 112 and the species 220. In other examples, the cover 130 is removed prior to the illumination of the Raman-active material nano-particles 112 and the species 220. In any regard, and by way of example, the illumination source 202 comprises a laser that illuminates the substance 210 and the Raman-active material nano-particles 112. Illumination of the Raman-active material nano-particles 112 causes hot spots of relatively large electric field strength to occur. The hot spots are increased at the locations where the Raman-active material nano-particles 112 contact each other. The electric fields generated at the contact locations between the Raman-active material nano-particles 112 generally enhance the rate at which Raman light is scattered by the species 220 positioned at or near the contact locations. The Raman scattered light, which is represented by the arrow 208, is shifted in frequency by an amount that is characteristic of particular vibrational modes of the species 220. The detector 204 is to collect the Raman scattered light 208 and spectral analysis is to be performed on the Raman scattered light 208.

The Raman-active material nano-particles 112 located near or adjacent to the species 220 is to enhance the production of Raman scattered light 208 from the species 220 by concentrating or otherwise enhancing an electromagnetic field in or around the species 220. In this regard, the likelihood that the species 220 will produce sufficiently strong Raman scattered light 208 to be detected by the detector 204 and processed will thus also be increased.

Although the Raman scattered light 208 has been depicted as being directed toward the detector 204, the Raman scattered light 208 is emitted in multiple directions. In this regard, some of the Raman scattered light 208 may be directed into the body 202, which, in one example, comprises an optical waveguide. More particularly, for instance, Raman scattered light 208 may be generated in the body 102 as a result of the species 220 coupling to the evanescent field of a waveguide mode. In these instances, the detector 204 may be positioned to detect the waves generated in the body 102 from the Raman scattered light 208. In any regard, the detector 204 may include a filter to filter out light originating from the illumination source 202, for instance, through use of a grating-based monochrometer or interference filters. The detector 204 may alternatively be positioned at other locations with respect to the nano-fingers 110, for instance, below the body 102 in FIG. 2.

In any regard, the detector 204 is generally to convert the Raman scattered light 208 emitted from the species 220 into electrical signals. In some examples, the detector 204 is to output the electrical signals to other components (not shown) that are to process the electrical signals, such as, a computing device. In other examples, the detector 204 is equipped with the processing capabilities.

According to an example, the illumination source 202, the detector 204, and other components of the sensing device 200 that have not been shown herein, such as, a CPU, a power supply, a battery, user interface, etc., are contained within a housing 230. In this example, the sensing device 200 is usable outside of a laboratory environment, and therefore, is to be used, for instance, at a location where the sample fluid is obtained.

In further examples, the apparatus 100 is removably inserted into the sensing device 200. In these examples, the apparatus 100 may comprise a disposable unit and the sensing device 200 may be reused multiple times to perform sensing operations on apparatuses 100 containing different samples.

Figure 3:
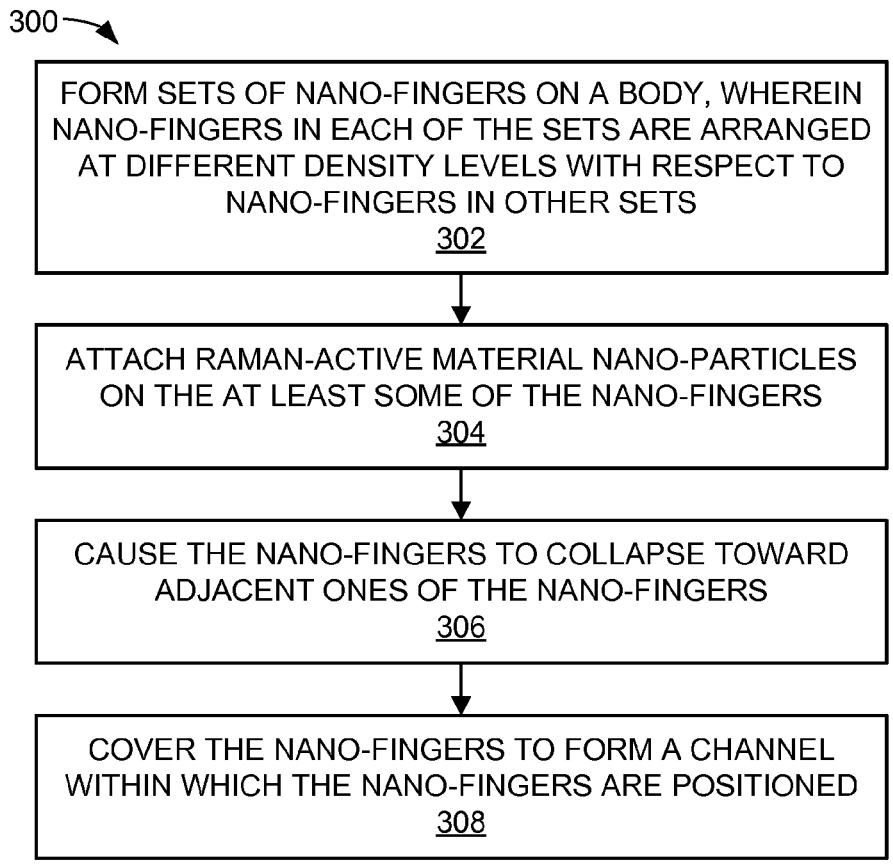
FIG. 3 shows a flow diagram of a method for fabricating the apparatus depicted in FIG. 1A, according to an example of the present disclosure.

Turning now to FIG. 3, there is shown a flow diagram of a method 300 for fabricating an apparatus 100 for filtering species in a fluid, according to an example. It should be understood that the method 300 may include additional processes and that some of the processes described herein may be removed and/or modified without departing from a scope of the method 300.

At block 302, sets 120, 122 of nano-fingers 110 are formed on a body 102, in which the nano-fingers 110 in each of these sets 120, 122 are arranged at different density levels with respect to nano-fingers 110 in other sets 120, 122. According to an example, the density levels are to gradually increase from one side 104 of the body 102 to the other side 106 of the body 102, to thereby filter gradually smaller species as the fluid flows from one side to the other.

In any regard, and according to an example, a nanoimprinting technique or a roll-to-roll process is implemented to form the nano-fingers 110 on the surface of the body 102. In this example, a template may be formed through photolithography or other advanced lithography with the desired patterning to arrange the nano-fingers 110 in the predetermined arrangement. More particularly, for instance, the desired patterns may be designed on a mold, by E-beam lithography, photolithography, laser interference lithography, Focused Ion Beam (FIB), self-assembly of spheres, etc. In addition, the pattern may be transferred onto, for instance, silicon, glass, or polymer substrate (PDMS, polyimide, polycarbonate, etc.). In other examples, the nano-fingers 110 may be formed in the predetermined or substantially random arrangement through implementation of any suitable fabrication process. In addition, the nano-fingers 110 may be provided on the surface of the body 102 through any suitable attachment mechanism as discussed above.

At block 304, Raman-active material nano-particles 112 are attached to at least some of the nano-fingers 110. More particularly, Raman-active material nano-particles 112 are attached to at least some of the nano-fingers 110 as discussed above with respect to FIG. 1B. The atoms or atom clusters of the Raman-active material nano-particles 112 may be deposited onto the selected nano-fingers 110 through, for instance, physical vapor deposition (PVD), chemical vapor deposition (CVD), sputtering, etc., of metallic material, or self-assembly of pre-synthesized nano-particles.

At block 306, the nano-fingers 110 are caused to collapse toward each other such that tips of the nano-fingers 110 are substantially in contact with each other. According to an example, the nano-fingers 110 are initially in a first position, in which their tips are in a substantially spaced arrangement with respect to each other. In addition, the gaps between the tips of the nano-fingers 110 are of sufficiently large size to enable a liquid to be supplied in the gaps. Moreover, the gaps are of sufficiently small size to enable the tips of the nano-fingers 110 to move toward each other as the liquid evaporates, through, for instance, capillary forces applied on the tips as the liquid dries. Other non-limiting examples, such as e-beam, ion-beam, magnetic, mechanical force, thermal effect, or electric charge effect, may also or instead be utilized to cause the tips of the nano-fingers 110 to move toward each other. In any regard, the Raman-active material nano-particles 112 may contact each other and remain in contact with each other through, for instance, van der Waals interactions between those contacting nano-particles 112.

At block 308, the nano-fingers 110 are covered with a cover 130, in which the cover 130 forms a channel with the base 102 within which the nano-fingers 110 are positioned. According to an example, the cover 130 comprises a prefabricated substantially u-shaped structure and the legs of the cover 130 are attached to a surface of the base 102 in any suitable manner as discussed above.

Figure 4:
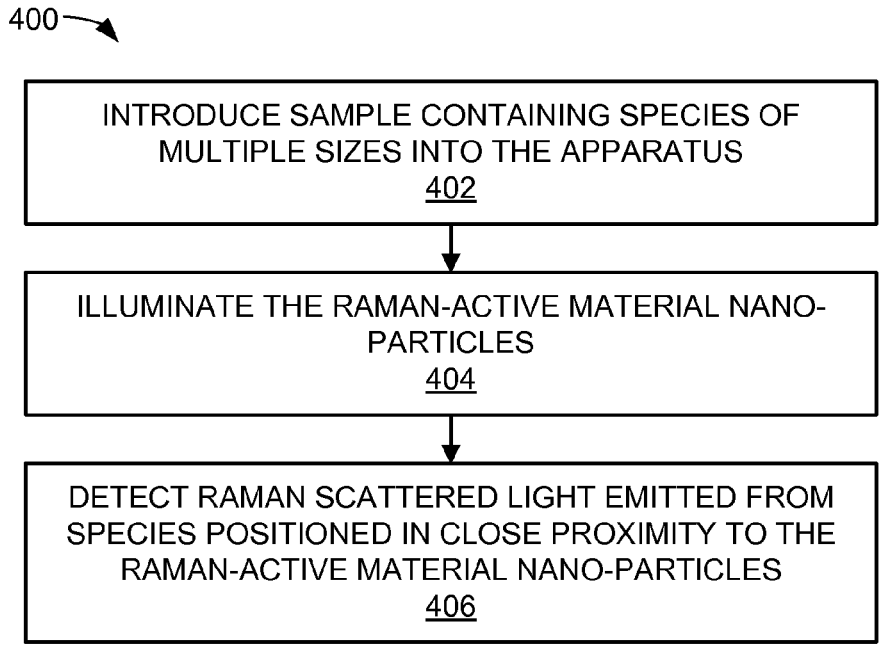
FIG. 4 shows a flow diagram of a method for performing a sensing operation using the apparatus depicted in FIGS. 1A-1D, according to an example of the present disclosure.

Turning now to FIG. 4, there is shown a flow diagram of a method 400 for performing a sensing operation using the apparatus 100 depicted in FIGS. 1A-1D, according to an example. It should be understood that the method 400 may include additional processes and that some of the processes described herein may be removed and/or modified without departing from a scope of the method 400.

At block 402, a sample containing species of multiple sizes is introduced into the apparatus 100. More particularly, for instance, the fluid sample is introduced into the first side 104 of the apparatus 102. In addition, the fluid sample is caused to move through the apparatus 100, while being filtered by the nano-fingers 110. More particularly, relatively smaller sized species 220 in the fluid sample are able flow though the gaps 150 between the nano-fingers 110 in the first set 120, while relatively larger sized species 220 are trapped in the gaps 150. In certain implementations, the fluid sample moves through the apparatus 100 because of capillary forces acting on the fluid sample. In other implementations, the fluid sample is forced through the apparatus 102, for instance, through use of microfluidic pumps, piezoelectric devices, etc.

At block 404, the Raman-active material nano-particles 112 and the species 220 in at least one of the first set 120 and the second set 122 of nano-fingers 110 are illuminated, for instance, by the illumination source 202. In one example, the illumination source 202 directs light 206 through the cover 130 and onto the Raman-active material nano-particles 112 and the species 220. In another example, the cover 130 is removed prior to illumination of the Raman-active material nano-particles 112 and the species 220. In this example, the sensing device 200 may be equipped with a mechanism (not shown) for removing the cover 130, without substantially damaging the nano-fingers. In any regard, illumination of the Raman-active material nano-particles 112 and the species 220 causes Raman scattered light to be emitted by the species 220.

At block 406, the Raman scattered light emitted from the species 220 positioned in close proximity to the Raman-active material nano-particles 112 is detected, for instance, by the detector 204. Moreover, the detector 204 may generate electrical signals corresponding to the Raman scattered light, which may be used to detect at least one characteristic of the species 220.

According to an example, the method 400 is repeated for different sections of the apparatus 100. In this example, the Raman-active material nano-particles 112 and the species 220 located in different subsets of the second set 122 of nano-fingers 110 are tested during different iterations of the method 400. In addition, or alternatively, the Raman-active material nano-particles 112 and the species 220 located in different sets 120, 124 of the nano-fingers 110 are tested during different iterations of the method 400. As a further example, the apparatus 100 may be removed and replaced with another apparatus 100, and the method 400 may be performed on the new apparatus 100.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. An apparatus for filtering species in a fluid, said apparatus comprising:
   a body having a first side and a second side;
   a first set of nano-fingers positioned on the body near the first side;
   a second set of nano-fingers positioned on the body closer to the second side than the first set of nano-fingers, wherein the nano-fingers in the second set of nano-fingers are arranged on the body relatively more densely than the nano-fingers in the first set of nano-fingers, wherein the second set of nano-fingers comprises a plurality of subsets of nano-fingers, and wherein at least two of the subsets of nano-fingers are functionalized differently from each other;
   a cover positioned over the first set of nano-fingers and the second set of nano-fingers to form a channel with the body, the first and second sets of nano-fingers being positioned within the channel; and
   a plurality of chambers, wherein the differently functionalized subsets of nano-fingers are positioned in respective ones of the plurality of chambers.

2. The apparatus according to claim 1, wherein the nano-fingers in the first set and the second set are composed of a flexible material, and wherein the nano-fingers are collapsed toward each other such that a plurality of the nano-fingers in the first set are substantially in contact with adjacent ones of the nano-fingers in the first set and a plurality of the nano-fingers in the second set are substantially in contact with adjacent ones of the nano-fingers in the second set.

3. The apparatus according to claim 1, wherein, at least one of:
   the first set of nano-fingers comprises a fewer number of nano-fingers per unit of space as compared with the second set of nano-fingers over the same unit of space; and
   the first set of nano-fingers comprises relatively thinner nano-fingers as compared with the nano-fingers in the second set.

4. The apparatus according to claim 1, further comprising:
   a third set of nano-fingers positioned on the body between the first set and the second set of nano-fingers, wherein the third set of nano-fingers are arranged on the body to have a density level between the density levels of the first set of nano-fingers and the second set of nano-fingers.

5. The apparatus according to claim 1, wherein the first set of nano-fingers and the second set of nano-fingers are arranged on the body to cause gaps between the nano-fingers in the respective first and second sets of nano-fingers to have substantially predetermined sizes.

6. The apparatus according to claim 1, wherein the cover is formed of an optically transparent material.

7. The apparatus according to claim 1, further comprising:
   Raman-active material nano-particles attached to at least one of the first set of nano-fingers and the second set of nano-fingers.

8. A sensing device to perform a sensing application on the apparatus of claim 7, said sensing device comprising:

an illumination source to illuminate the Raman-active material nano-particles and species of the fluid; and a detector positioned to detect Raman scattered light emitted from the species positioned in close proximity to the Raman-active material nano-particles.

9. The sensing device according to claim 8, wherein the apparatus is integrated with the illumination source and the detector.

10. A method for fabricating the apparatus of claim 7, said method comprising:

forming the first set and the second set of nano-fingers on the body to have different density levels with respect to each other;

attaching the Raman-active material nano-particles onto the nano-fingers of at least one of the first set and the second set of nano-fingers;

causing the nano-fingers to collapse toward adjacent ones of the nano-fingers; and covering the first set and the second set of nano-fingers with the cover.

11. A method for performing a sensing operation using the apparatus of claim 7, said method comprising:

introducing a sample containing species of multiple sizes to be tested into the apparatus, wherein the sample is caused to flow from the first side of the body toward the second side of the body, and wherein relatively smaller sized species in the sample are able to flow through the first set of nano-fingers while relatively larger sized species are trapped in gaps between the first set of nano-fingers;

illuminating the Raman-active material nano-particles and the species on at least one of the first set and the second set of nano-fingers; and detecting Raman scattered light emitted from species positioned in close proximity to the Raman-active material nano-particles.

12. The method according to claim 11, further comprising removing the cover prior to illuminating the Raman-active material nano-particles and the species.

13. The apparatus of claim 1, wherein the channel is tapered as it extends from the first side to the second side of the body.

* * * * *